US008021383B2

(12) United States Patent
Zhong

(10) Patent No.: US 8,021,383 B2
(45) Date of Patent: Sep. 20, 2011

(54) SINGLE-HANDED, REDUCED VIBRATION LANCING DEVICE

(75) Inventor: Weiping Zhong, Granger, IN (US)

(73) Assignee: Bayer HealthCare LLC, Tarrytown, NY (US)

(*) Notice: Subject to any disclaimer, the term of this patent is extended or adjusted under 35 U.S.C. 154(b) by 365 days.

(21) Appl. No.: 12/224,475

(22) PCT Filed: Mar. 9, 2007

(86) PCT No.: PCT/US2007/006098
§ 371 (c)(1),
(2), (4) Date: Aug. 27, 2008

(87) PCT Pub. No.: WO2007/108967
PCT Pub. Date: Sep. 27, 2007

(65) Prior Publication Data
US 2009/0054920 A1    Feb. 26, 2009

Related U.S. Application Data

(60) Provisional application No. 60/782,474, filed on Mar. 15, 2006.

(51) Int. Cl.
*A61B 17/34* (2006.01)
(52) U.S. Cl. ...................................................... 606/182
(58) Field of Classification Search .......... 606/181–188, 606/167–170; 600/583, 584
See application file for complete search history.

(56) References Cited

U.S. PATENT DOCUMENTS

| | | | |
|---|---|---|---|
| 4,503,856 A | 3/1985 | Cornell et al. | 128/314 |
| 4,527,561 A | 7/1985 | Burns | 128/314 |
| 4,535,769 A | 8/1985 | Burns | 128/314 |
| 4,553,541 A | 11/1985 | Burns | 128/314 |
| 4,643,189 A * | 2/1987 | Mintz | 606/182 |

(Continued)

FOREIGN PATENT DOCUMENTS

EP    1 074 219 A2    2/2001

(Continued)

OTHER PUBLICATIONS

Written Opinion corresponding to International Patent Application No. PCT/US2007/006098, European Patent Office, dated Sep. 21, 2007, 8 pages.

(Continued)

*Primary Examiner* — Elizabeth Houston
(74) *Attorney, Agent, or Firm* — Nixon Peabody LLP

(57) ABSTRACT

A lancing device includes a housing, at least two ramps, a lancet holder, a drive spring, and an activation mechanism. The housing includes first and second ends, and a first wall. The first end has an aperture extending therethrough and the first wall has an opening extending therethrough. The two ramps are located within the housing and forms a channel therebetween. The lancet holder is partially contained within the channel formed by the ramps and holds a lancet. The activation mechanism includes a user-accessible component and a plate spring. A portion of the user-accessible component extends through the opening and is external to the housing. The plate spring engages the ramps forming the channel and the lancet holder upon depression of the user-accessible component, the lancet holder moves towards the second end to a cocked position. Upon further depression of the user-accessible component, the lancet holder moves toward the first end to a puncture position.

15 Claims, 9 Drawing Sheets

U.S. PATENT DOCUMENTS

| | | | | |
|---|---|---|---|---|
| 4,735,203 | A | 4/1988 | Ryder et al. | 128/314 |
| 4,892,097 | A | 1/1990 | Ranalletta et al. | 606/182 |
| 4,895,147 | A | 1/1990 | Bodicky et al. | 606/182 |
| 4,976,724 | A | 12/1990 | Nieto et al. | 606/182 |
| 5,195,534 | A | 3/1993 | Sarrine | 128/764 |
| 5,318,584 | A | 6/1994 | Lange et al. | 606/182 |
| 5,350,392 | A | 9/1994 | Purcell et al. | 606/182 |
| 5,356,420 | A | 10/1994 | Czernecki et al. | 606/182 |
| 5,368,047 | A | 11/1994 | Suzuki et al. | 128/765 |
| 5,389,085 | A * | 2/1995 | D'Alessio et al. | 604/198 |
| 5,423,847 | A | 6/1995 | Strong et al. | 606/182 |
| 5,487,748 | A | 1/1996 | Marshall et al. | 606/182 |
| 5,628,764 | A | 5/1997 | Schraga | 606/182 |
| 5,741,288 | A | 4/1998 | Rife | 606/181 |
| 5,797,940 | A * | 8/1998 | Mawhirt et al. | 606/167 |
| 5,871,494 | A | 2/1999 | Simons et al. | 606/181 |
| 5,873,887 | A | 2/1999 | King et al. | 606/182 |
| 6,042,595 | A * | 3/2000 | Morita | 606/181 |
| 6,045,567 | A | 4/2000 | Taylor et al. | 606/181 |
| 6,152,942 | A | 11/2000 | Brenneman et al. | 606/181 |
| 6,197,040 | B1 | 3/2001 | LeVaughn et al. | 606/182 |
| 6,221,089 | B1 * | 4/2001 | Mawhirt | 606/181 |
| 2005/0038464 | A1 | 2/2005 | Shraga | 606/182 |

FOREIGN PATENT DOCUMENTS

WO  WO 2004/039429 A2  5/2004

OTHER PUBLICATIONS

International Search Report corresponding to International Patent Application No. PCT/US2007/006098, European Patent Office, dated Sep. 21, 2007, 3 pages.

* cited by examiner

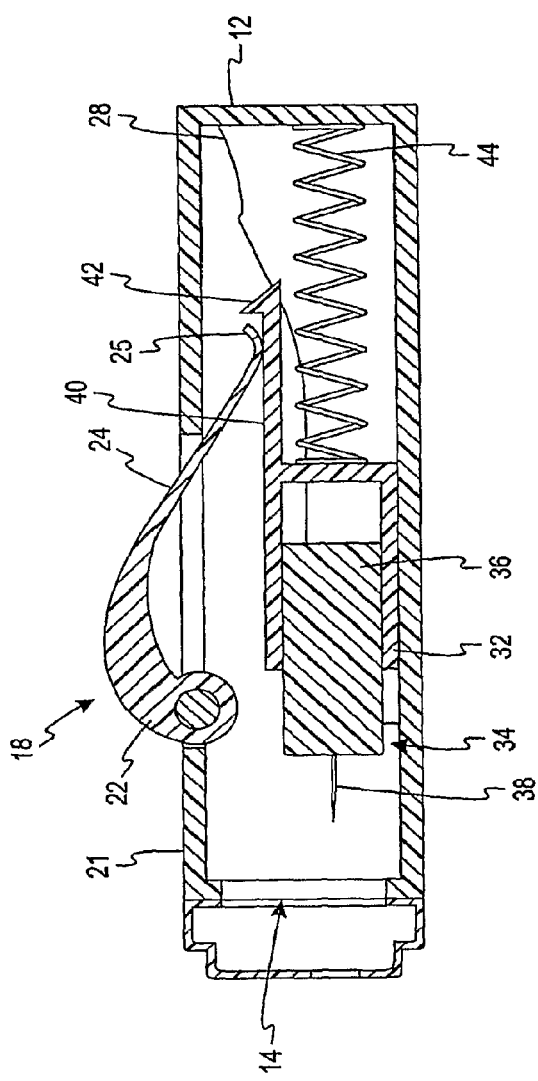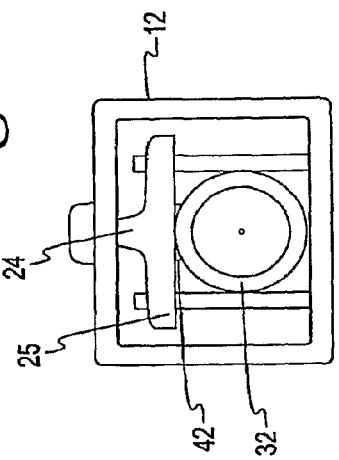
Fig. 3a
Fig. 3b

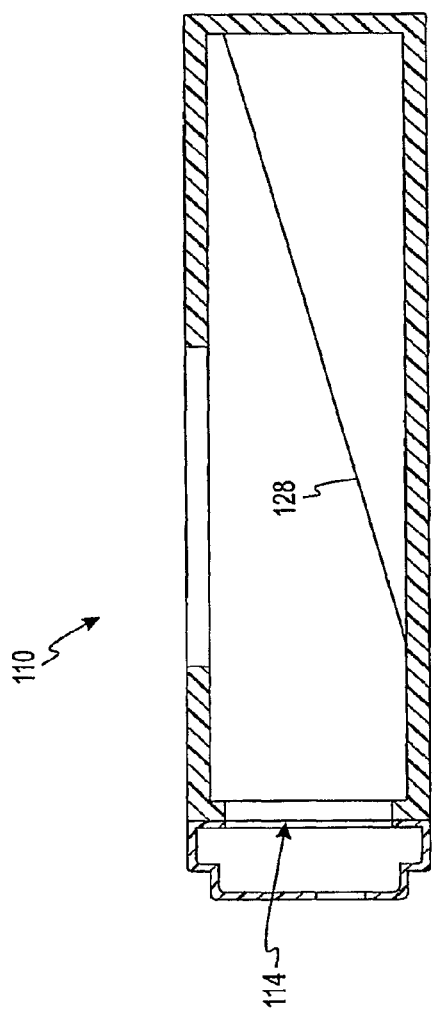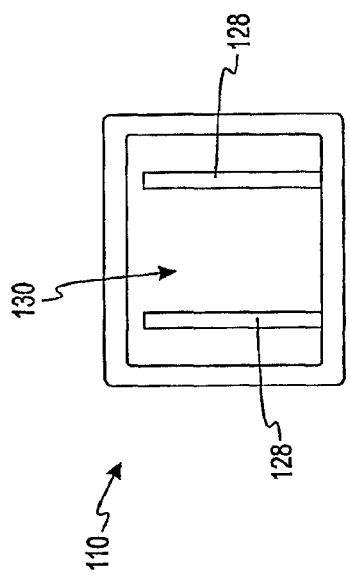

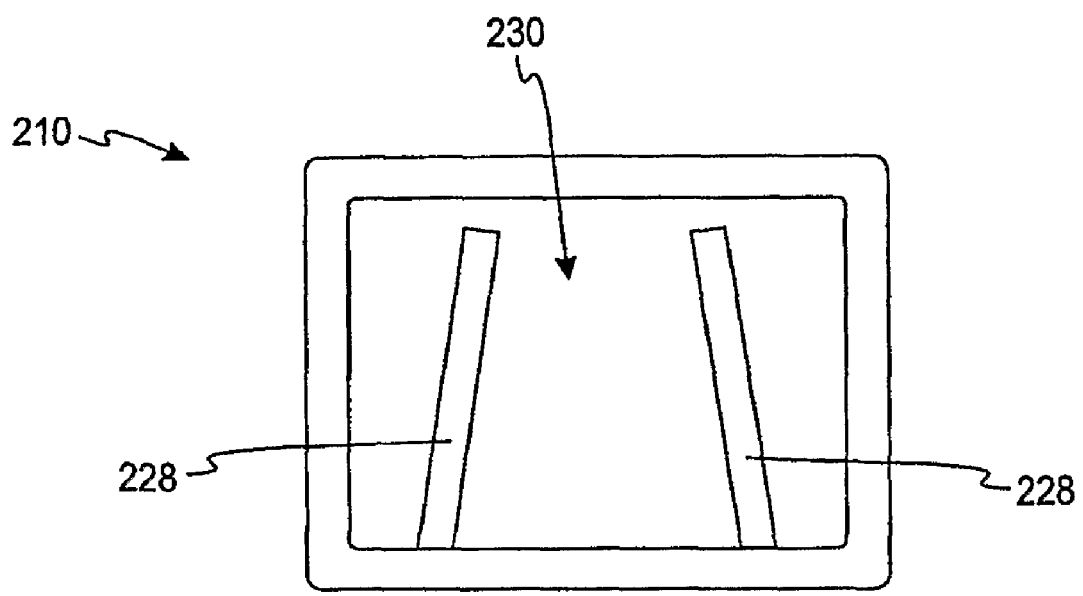
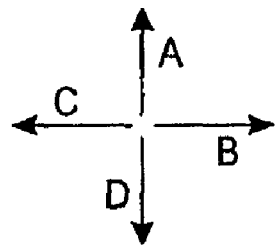
Fig. 6

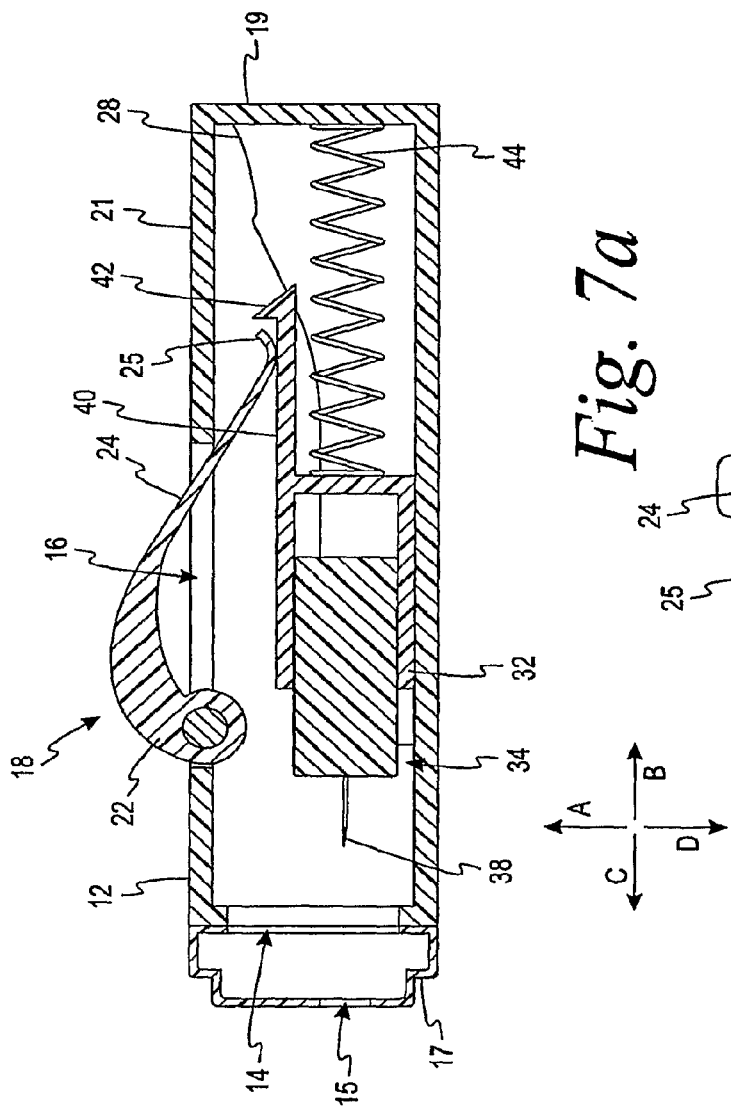
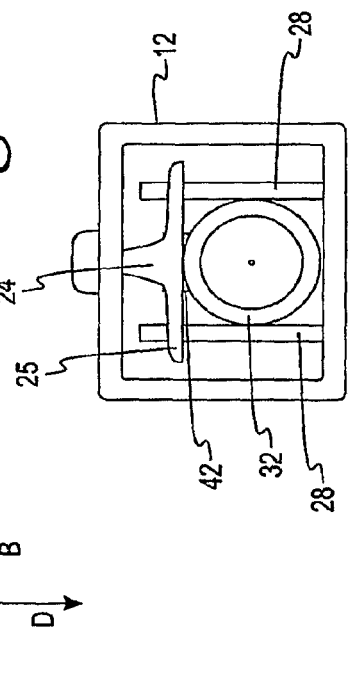
Fig. 7a
Fig. 7b

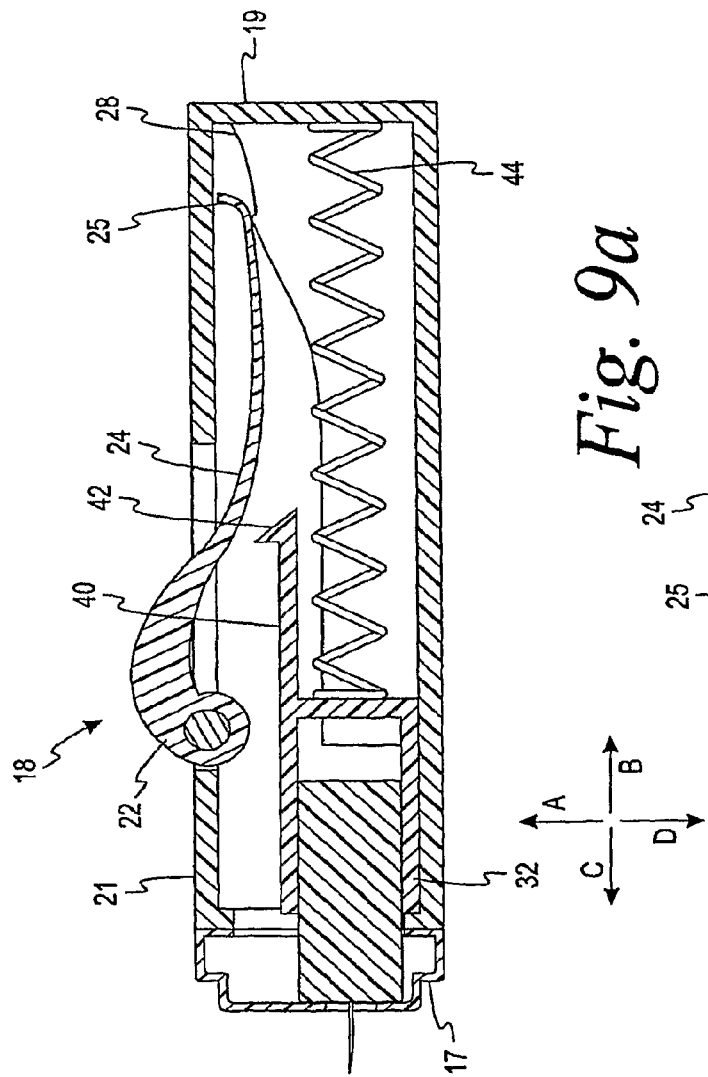
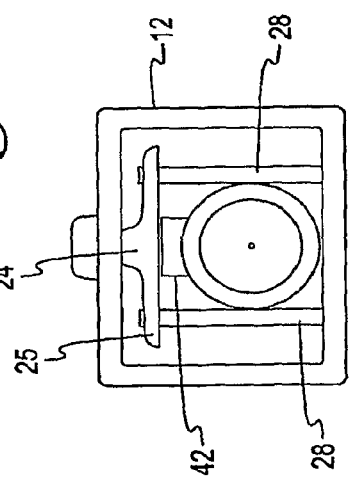
Fig. 9a
Fig. 9b

SINGLE-HANDED, REDUCED VIBRATION LANCING DEVICE

CROSS-REFERENCE TO RELATED APPLICATIONS

This application claims priority to Application No. 60/782,474 filed on Mar. 15, 2006, which is incorporated by reference in its entirety.

FIELD OF THE INVENTION

The present invention relates generally to lancing devices and, more particularly, to a system and method for allowing single-handed operation of a lancing device.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, determining glucose in body fluids is important to diabetic individuals who must frequently check their blood glucose levels to regulate the glucose intake in their diets.

One method of obtaining a body fluid sample, such as a whole blood sample, is to use a lancing device. The whole blood sample may then be used to determine the glucose concentration of an individual. Existing lancing devices use a lancet to pierce the tissue of the skin, allowing a blood sample to form on the skin's surface. Typically, lancing devices hold the lancet within them when the lancet is not in use, so as to shield the user from injury as well as to assist in preventing or inhibiting contamination.

Existing lancing devices typically require two-handed operation and can be dangerous. Two-handed operation requires that a user use one hand to hold the lancing device while the other hand activates the lancing device. Furthermore, the activation of lancing devices are typically done in at least two steps—cocking the device and firing the device. This is inconvenient to many users as the user does not have the use of another hand while operating the lancing device. Additionally, the two-step process of activating a lancing device causes safety issues because once cocked, a user may inadvertently fire the lancing device. By inadvertently firing a lancing device, one may unintentionally pierce one's or another's skin causing pain and discomfort or the transmittal of diseases.

It would be desirable to have a lancing device and a method for using a lancing device that addresses these issues.

SUMMARY OF THE INVENTION

A lancing device is disclosed according to one embodiment of the present invention. The lancing device includes a housing, a lancet holder, a drive spring, and an activating mechanism. The housing forms a central cavity and includes an aperture and an opening. The aperture has an axis aligned in a first direction and the opening has an axis aligned in a second direction. The first direction is generally perpendicular to the second direction. The lancet holder is located within the central cavity formed by the housing. The lancet holder is adapted to receive and maintain a lancet in a position generally aligned with the aperture. The lancet is adapted to at least partially extend through the aperture. The drive spring attaches to and connects the lancet holder opposite the aperture, and the housing. The activating mechanism includes a user-accessible component and a plate spring. At least a portion of the user-accessible component extends through the opening external to the housing and is adapted to be depressed in the second direction towards the housing. The plate spring is adapted to engage the lancet holder upon depression of the user-accessible component in the second direction. The depression of the user-accessible component in the second direction causes the plate spring to move the lancet holder away from the aperture in the first direction to a cocked position.

A lancing device is disclosed according to another embodiment of the present invention. The lancing device includes a housing, at least two ramps, a lancet holder, a drive spring, and an activation mechanism. The housing includes a first end, a second end, and a first wall. The first end is adjacent to the first wall. The second end is also adjacent to the first wall, opposite the first end. The first end has an aperture extending therethrough and the first wall has an opening extending therethrough. The at least two ramps are located within the housing forming a channel therebetween generally aligned with the aperture. The lancet holder is partially contained within the channel formed by the ramps and is adapted to hold a lancet in a position generally aligned with the aperture. The drive spring is attaches to and connects the lancet holder opposite the aperture, and the second end of the housing. The activation mechanism includes a user-accessible component and a plate spring. At least a portion of the user-accessible component extends through the opening and is external to the housing. The plate spring is substantially located within the housing and is adapted to engage the ramps forming the channel as well as the lancet holder upon depression of the user-accessible component in the direction of the housing. In response to depression of the user-accessible component, the lancet holder is adapted to move towards the second end to a cocked position. Upon further depression of the user-accessible component, the lancet holder is adapted to move toward the first end to a puncture position.

A method for using a lancing device is disclosed according to one embodiment of the present invention. The method includes the act of depressing an activation mechanism in a first direction. The activation mechanism includes a user-accessible component and a plate spring. The method further includes the act of moving a lancet holder in a second direction to a cocked position. The second direction is generally perpendicular to the first direction. The depression of the activation mechanism in the first direction causing the plate spring to engage the lancet holder. The method further including the act of releasing the lancet holder. The release of the lancet holder allows the lancet holder to move in a third direction to a puncture position. The third direction is opposite the second direction.

The above summary of the present invention is not intended to represent each embodiment, or every aspect, of the present invention. Additional features and benefits of the present invention are apparent from the detailed description and figures set forth below.

BRIEF DESCRIPTION OF THE DRAWINGS

FIG. 3a is a cross-sectional side view of a portion of the lancing device of FIG. 1.

FIG. 3b is a cross-sectional end view of the portion of the lancing device illustrated in FIG. 3a without the endcap.

FIG. 5a is an end view of a portion of a lancing device according to another embodiment.

FIG. 5b is a cross-sectional end view of the portion of the lancing device of FIG. 5a without the endcap.

FIG. 6 is an end view of a portion of a lancing device according to yet another embodiment of the present invention.

FIG. 7a is a cross-sectional side view of the lancing device of FIG. 1 in a resting position.

FIG. 7b is an end view of the lancing device of FIG. 7a without the endcap.

FIG. 9a is a cross-sectional side view of the lancing device in a puncture position.

FIG. 9b is an end view of the lancing device illustrated in FIG. 9b without the endcap.

DESCRIPTION OF ILLUSTRATED EMBODIMENTS

The present invention is directed to a lancing device for obtaining a body fluid sample from a test subject. The body fluid generally contains at least one analyte that may then be examined to determine its concentration in the body fluid sample. For example, this sample may be analyzed with a meter and test strip, or similar devices, to determine the concentration of the analyte to be examined. Examples of the types of analytes that may be collected with a lancing device include glucose, lipid profiles (e.g., cholesterol, triglycerides, LDL and HDL), microalbumin, hemoglobin $A_{IC}$, fructose, lactate, or bilirubin.

Figure 1:
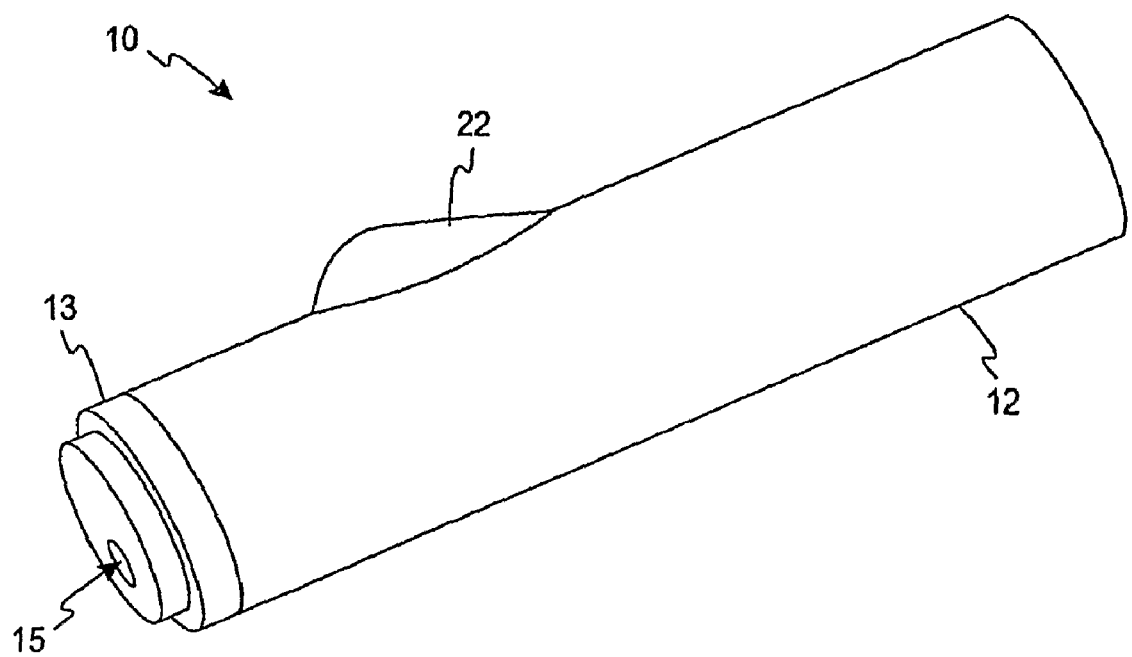
FIG. 1 is a perspective view of a lancing device according to one embodiment of the present invention.
Figure 2:
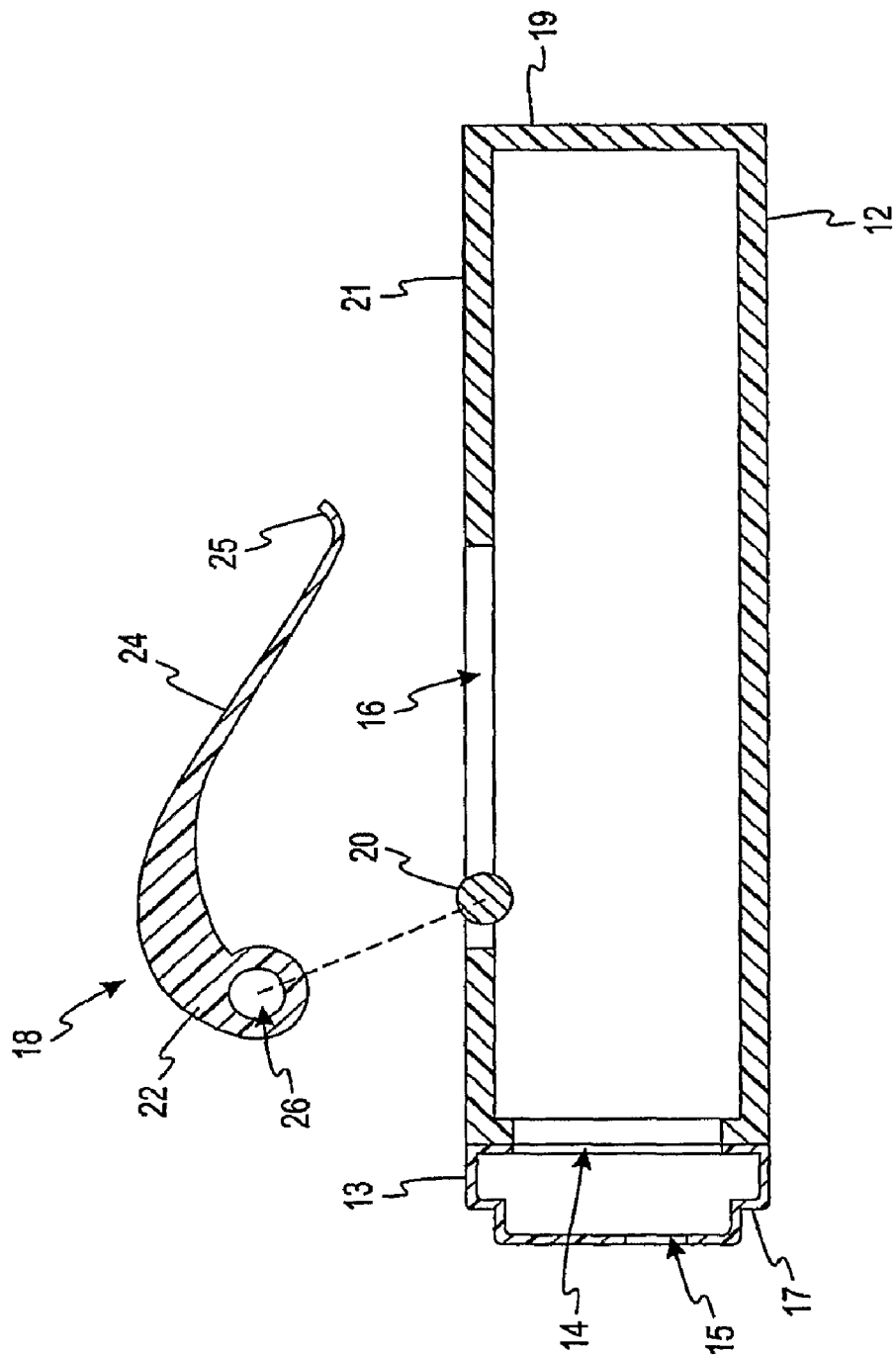
FIG. 2 is an exploded cross-sectional side view of a portion of the lancing device of FIG. 1.

Turning now to the drawings and initially to FIGS. 1-2, a lancing device 10 for obtaining a fluid sample from a test subject is illustrated, according to one embodiment of the present invention. The lancing device 10 includes a housing 12 and an endcap 13 adapted to be removeably attached to the housing 12. The endcap 13 covers an aperture 14 on a first end 17 of the lancing device 10 and includes a lancet aperture 15 adapted to allow a lance 38 of a lancet 34 (FIGS. 3a-3b) to extend therethrough. The housing 12 forms an opening 16 on a first wall 21 of the lancing device 10. The opening 16 is adapted to receive an activation mechanism 18 for the lancing device 10. A pin 20, adapted to secure the activation mechanism 18 to the housing 12, may be provided and may partially extend through the opening 16. However, other suitable attachment methods may be used. It should be noted that the lancing device 10, as illustrated in FIG. 2, omits certain components for purposes of clarity in describing the components shown therewithin.

The activation mechanism 18 includes a user-accessible component 22 and a plate spring 24 that are molded to form the activation mechanism 18. In other embodiments, the user-accessible component and the plate spring may be fabricated separately and subsequently molded together. Accordingly, the user-accessible component and the plate spring may be attached via molding. The user-accessible component and the plate spring may also be attached using any suitable means so long as the activation mechanism 18 functions as will be described below. Alternatively, the user-accessible component and the plate spring may also be manufactured as a single component.

The user-accessible component 22 may form a hole 26 adapted to receive the pin 20. The hole 26 and the pin 20 enable a partially rotatable attachment between the activation mechanism 18 and the housing 12. It is contemplated that other attachment means may be implemented. However, the attachment methods of the activation mechanism and the housing should enable traverse movement of a portion of the activation mechanism with respect to the housing.

Figure 8A:
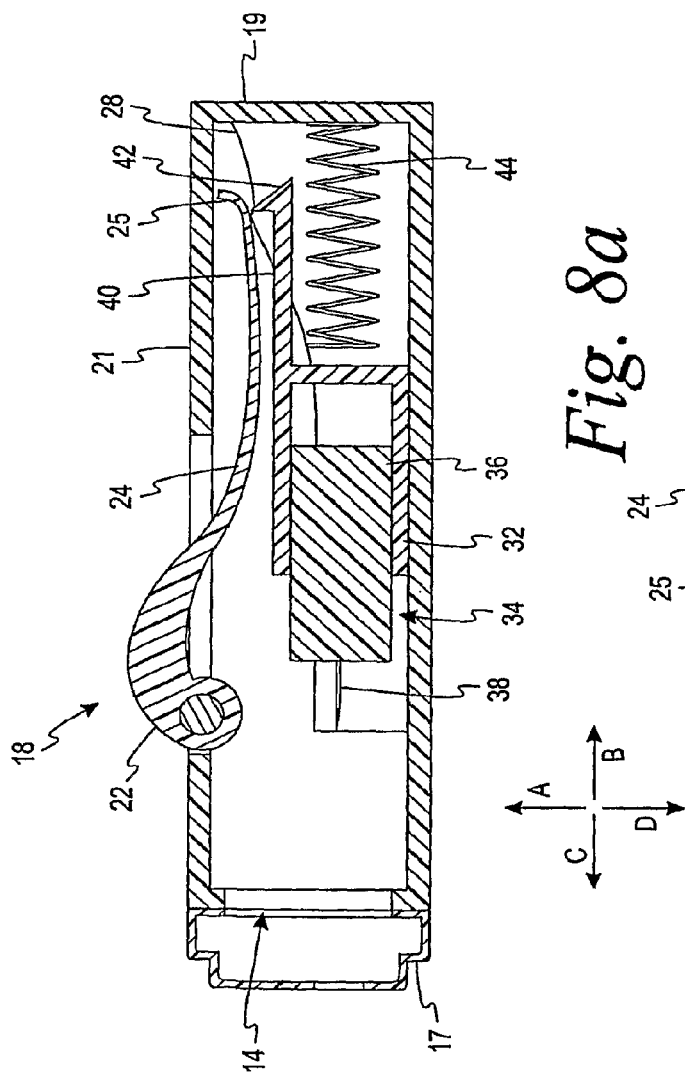
FIG. 8a is a cross-sectional side view of the lancing device in a cocked position.
Figure 8B:
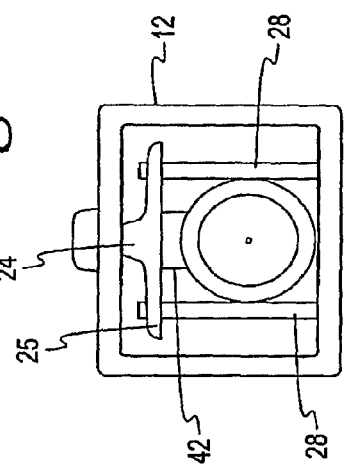
FIG. 8b is an end view of the lancing device illustrated in FIG. 8a without the endcap.

The plate spring 24 is comprised of a generally flexible material such that the plate spring 24 is capable of at least minimal deformation. Accordingly, some materials that may be used for the plate spring 24 include, but are not limited to, copper, steel, and stainless steel. The plate spring 24 is adapted to associate with a lancet holder 32 (see, e.g., FIG. 3a) and ramps 28 (see, e.g., FIG. 9a), both of which being located within the housing 12. In the illustrated embodiment, the plate spring 24 includes a lip 25 that facilitates the engagement of the plate spring 24 with the lancet holder 32 and the ramps 28, as will be described below with respect to FIGS. 7-9.

Turning now to FIGS. 3a and 3b, the lancing device 10 as illustrated in FIGS. 3a and 3b also omits certain components for purposes of clarity in describing the components shown therewithin. The lancet holder 32 is located within the housing 12 and is generally aligned with the aperture 14. The lancet holder 32 is adapted to receive the lancet 34. The lancet 34 is formed by a body 36 with the lance 38 extending therefrom. The lance 38 is adapted to puncture the skin of a test subject when the lancet holder 32 is moved from a cocked position (illustrated in FIGS. 8a and 8b) to a puncture position (illustrated in FIGS. 9a and 9b). As illustrated, the lancet holder 32 may include an extension 40 extending therefrom opposite the lance 38. In some embodiments, the extension 40 facilitates the engagement between the plate spring 24 and the lancet holder 32. In embodiments where the extension 40 is utilized, the particular length of the extension 40 may vary depending on the particular design characteristics so as to enable the device to function as will be described below.

The extension 40 may include an endpiece 42. In an alternative embodiment where an extension is not utilized, the lancet holder 32 may nonetheless include an endpiece that extends directly from the lancet holder 32. The endpiece 42 assists in inhibiting the premature disengagement of the plate spring 24 from the lancet holder 32. As mentioned above, the lip 25 of the plate spring 24 aids the engagement of the lancet holder 32. Accordingly, it is desirable that the lip 25 and the endpiece 42 are formed to enable a removeable attachment therebetween. In the illustrated embodiment, the lip 25 of the plate spring 24 may include a bend in the plate spring 24, opposite the user-accessible component 22, so as to allow for easier disengagement of the plate spring 24 from the lancet holder 32. The lip 25 extends a sufficient distance from the plate spring 24 to contact the ramps 28 (as illustrated in FIG. 7b) and provide a larger surface for contacting the endpiece 42. Similarly, the endpiece 42, and in some embodiments the extension 40; provides a suitable contact surface for the lancet holder 32 to be engaged by the plate spring 24. The lip 25 and the endpiece 42 may be shaped differently than shown in the FIGS. The embodiments illustrated are provided by way of example only and any suitable shape of the lip 25 and the endpiece 42 that enables removeable attachment therebetween and allows the components to function as described is contemplated for use.

Figure 4A:
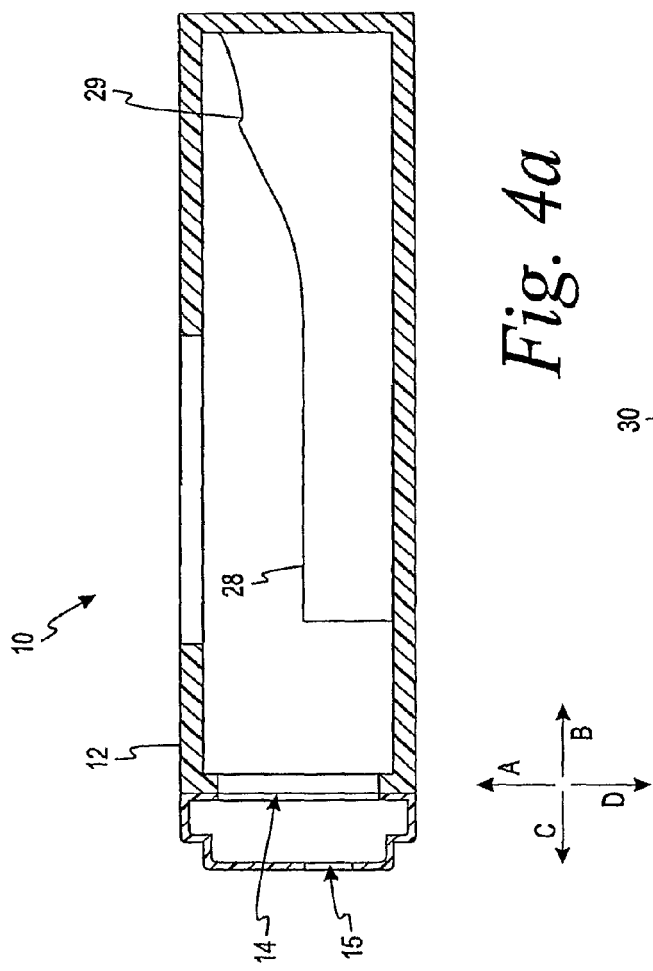
FIG. 4a is an end view of a portion of the lancing device of FIG. 1.
Figure 4B:
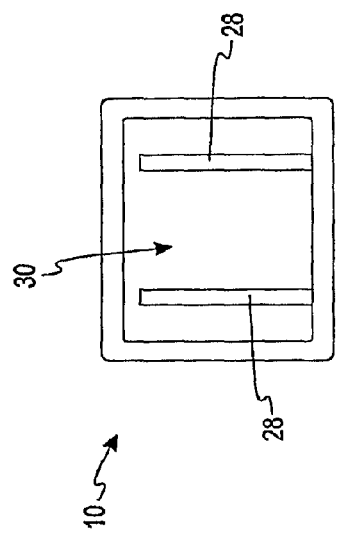
FIG. 4b is a cross-sectional end view of the potion of the lancing device illustrated in FIG. 4a without the endcap.

As mentioned above, the lip 25 should also enable engagement of the plate spring 24 with the ramps 28. For purposes of clarity, FIGS. 4a and 4b show the ramps 28 in the housing 12 without the other components included therewith (e.g., lancet holder 32, activation mechanism 18). The ramps 28 are adapted to facilitate the disengagement of the plate spring 24 from the lancet holder 32. In doing so, the ramps 28 are adapted to permit the lancet holder 32 to move from the cocked position (illustrated in FIGS. 8a and 8b) to the puncture position (illustrated in FIGS. 9a and 9b).

As can be seen in FIG. 4b, the ramps 28 are generally parallel to one another and form a channel 30 therebetween. The lancet holder 32 is generally located within the channel 30 (shown in FIG. 7b). In this illustrated embodiment, the ramps 28 are generally aligned with the aperture 14 and may direct the lance 38 of the lancet 34 through the lancet aperture 15 as the lancet holder 32 moves from the cocked position to the puncture position. As the distance from the aperture 14 within the housing 12 increases, the ramps 28 generally trend in the direction of arrow A (as shown in FIG. 4a). As illustrated in FIG. 4a, the trend may be generally curvilinear in nature. At a certain distance from the aperture 14, the ramps 28 reach a threshold distance away from the extension 40 of the lancet holder 32 in the direction of arrow A. Generally, the threshold distance is where the ramps 28 are further than the extension 40 in the direction of arrow A so that the plate spring 24 disengages the lancet holder 32 and only engages the ramps 28 (see FIG. 9a).

An alternative embodiment of a lancing device 110 that includes a plurality of ramps 128 is shown in FIGS. 5a and 5b. Again, it should be noted that the illustration omits certain components for purposes of clarity. In this embodiment, as the distance from an aperture 114 increases, the ramps 128 proportionately slope linearly in the direction of arrow A. In this embodiment, the ramps 128 are generally parallel as shown in FIG. 5b. Accordingly, a lancet bolder (e.g., 32) remains located within a channel 130. According to another embodiment, illustrated in FIG. 6, a lancing device 210 includes a plurality of ramps 228 that are not parallel. The ramps 228 may approach the direction of arrow A similar to the ramps 28 or the ramps 128 (i.e., curvilinearly or linearly). A lancet holder (e.g., lancet holder 32) may be located in a channel 230 formed by the ramps 228. The movement of the lancet holder toward an aperture (e.g., aperture 14) would not be prevented by the ramps 228. The dimensions of the ramps 228 enable the disengagement of a plate spring (e.g., plate spring 24) from the lancet holder as described above, thereby facilitating the lancet holder to move from the cocked position (FIGS. 8a and 8b) to the puncture position (FIGS. 9a and 9b). Similar to the previously described embodiments, the ramps 228 are adapted to direct the lance 38 of the lancet 34 through the lancet aperture 15. It should be noted that the ramps can be of any reasonable form as to enable a lancing device (e.g., 10) to function as will be described below with respect to FIGS. 7-9.

Referring now to FIGS. 7a and 7b, a drive spring 44 located within the housing 12 is provided to facilitate the movement of the lancet holder 32 from the cocked position to the puncture position. One end of the drive spring 44 is attached to the housing 12 at a second end 19 opposite the first end 17. The other end of the drive spring 44 is attached to the lancet holder 32. The drive spring 44 is adapted to be compressed in the direction opposite the aperture 14 (i.e., the direction of arrow B) as the plate spring 24 engages the lancet holder 32. Once the plate spring 24 is disengaged from the lancet holder 32 and only engaged with the ramps 28, the drive spring 44 is adapted to move the lancet holder 32 in the direction of arrow C to the puncture position.

As illustrated in FIGS. 7a and 7b, the lancing device 10 is shown in its resting position. To operate the lancing device 10, a user applies a force to the user-accessible component 22 generally towards the housing 12 in the direction of arrow D, which is parallel to a central axis of the opening 16. As the user-accessible component 22 begins to move towards the housing 12, the plate spring 24 moves along the extension 40 of the lancet holder 32 until the lip 25 of the plate spring 24 contacts the endpiece 42 of the extension 40.

As the user-accessible component 22 is further depressed, the lancet holder 32 begins to move in the direction of arrow B—away from the aperture 14. As the lancet holder 32 moves toward the second end 19 of the housing 12, the drive spring 44 becomes compressed between the lancet holder 32 and the housing 12. As the user-accessible component 22 continues to be depressed, the lancet holder 32 reaches the cocked position (illustrated in FIGS. 8a and 8b) and, upon further depression, the plate spring 24 disengages the lancet holder 32. After the endpiece 42 of the lancet holder 32 is disengaged from the plate spring 24, there is no longer a force being applied to the lancet holder 32 in the direction of arrow B. Accordingly, the compressed drive spring 44 is free to decompress and, as a result, applies a force on the lancet holder 32 in the direction of the aperture 14. Thus, the lancet holder 32 transitions from the cocked position (FIGS. 8a and 8b) to the puncture position (FIGS. 9a and 9b).

The transition from the cocked position to the puncture position occurs without any further user action aside from depressing the user-accessible component 22 until the lancing device 10 fires (i.e., the lancet holder 32 begins to move from the cocked position towards the puncture position). Accordingly, the lancing device 10 is fully functional upon a single user action—depressing the user-accessible component 22 in a direction generally perpendicular to the first wall 21 of the housing 12. However, the lancing device 10, in some embodiments, may include an additional user-accessible component (not illustrated). The lancing device 10, in such an embodiment, would include two functional user-accessible components—one for cocking the lancing device 10 and one for firing the lancing device 10.

At a certain distance from the aperture 14, as the lancet holder 32 approaches the second end 19 of the housing 12 and the drive spring 44 becomes compressed therebetween, the lip 25 of the plate spring 24 engages the ramps 28 as the ramps 28 trend in the direction of arrow A past the extension 40 of the lancet bolder 32. Once this initial engagement occurs, the lip 25 of the plate spring 24 continues contact with the ramps 28 as the ramps continue trending in the direction of arrow A. This results in the eventual disengagement of the plate spring 24 from the extension 40 of the lancet holder 32 at about the cocked position shown in FIGS. 8a and 8b. The disengagement allows the drive spring 44 to move the lancet holder 32 from the cocked position to the puncture position.

As the lancet holder 32 moves from the cocked position to the puncture position, the drive spring 44 fully decompresses and the momentum of the lancet holder 32 causes the drive spring 44 to extend past its resting position. Thus, after the lancet holder 32 has reached the puncture position, the lancet holder 32 is retracted, in the direction of arrow B, due to the return force of the drive spring 44. Upon retraction, the portion of the endpiece 42, opposite the aperture 14, contacts the plate spring 24. The portion of the endpiece 42 that comes into contact with the plate spring 24 upon retraction is adapted to enable the lancet holder 32 to continue in the direction away from the aperture 14 so that the endpiece 42 passes the lip 25 of the plate spring 24 at least a minimal distance towards the second end 19. In one embodiment, the endpiece 42 may have a substantially triangular cross-section, as illustrated.

The retraction force of the drive spring 44 causes the drive spring 44 to become partially compressed after retraction, thereby resulting in an additional force in the direction of the aperture 14 as the drive spring 44 partially decompresses. Unless inhibited, this additional force may result in multiple punctures of the test subject's skin by the lance 38 of the lancet 34. Accordingly, the lip 25 of the plate spring 24 is also adapted to operate as a dampening mechanism to inhibit multiple punctures. As the drive spring 44 decompresses and causes the lancet holder 32 to move back in the direction of the aperture 14, the lip 25 of the plate spring 24 contacts the endpiece 42 of the lancet bolder 32. The contact between the lip 25 and the endpiece 42 inhibits the lancet bolder 32 from continuing in the direction of the aperture 14 and thereby extending the lance 38 of the lancet 34 through the aperture 14. Thus, the activation mechanism 18 further acts as a dampening mechanism for the lancing device 10 as well as a cocking and firing mechanism.

An additional structural feature may be added to the ramps 28 to acoustically alert the user that the lancet holder 32 is transitioning from the cocked position to the puncture position. Accordingly, the ramps 28 may be uneven at about the point where the lancet holder 32 is disengaged from the plate spring 24, allowing the drive spring 44 to move the lancet holder 32 towards the aperture 14. The unevenness in the ramps 28 at this point creates a sound when the plate spring 24 contacts the uneveness. Referring back to FIG. 4a, a depression 29 is illustrated proximate the point of disengagement to create an audible notice. The acoustic alert may signal the user that they are about to fire the lancing device 10.

Alternate Embodiment A

A lancing device comprising:
a housing forming a central cavity including an aperture and an opening, the aperture including an axis aligned in a first direction and the opening includes an axis aligned in a second direction, the first direction being generally perpendicular to the second direction;
a lancet holder adapted to receive a lancet, the lancet holder being located within the central cavity formed by the housing, the lancet holder being adapted to maintain the lancet in a position generally aligned with the aperture, the lancet being adapted to at least partially extend through the aperture;
a drive spring attached to and connecting the lancet holder and the housing, the drive spring being attached to the lancet holder opposite the aperture; and
an activating mechanism including a user-accessible component and a plate spring, at least a portion of the user-accessible component extending through the opening and being external to the housing, the user-accessible component being adapted to be depressed in the second direction towards the housing, the plate spring being adapted to engage the lancet holder upon depression of the user-accessible component in the second direction,
wherein the depression of the user-accessible component in the second direction causes the plate spring to move the lancet holder away from the aperture in the first direction to a cocked position.

Alternate Embodiment B

The lancing device of alternative embodiment A, wherein the lancet holder includes an extension in the direction opposite the aperture, the plate spring being adapted to engage the extension upon depression of the user-accessible component.

Alternate Embodiment C

The lancing device of alternative embodiment B, wherein the extension includes an endpiece, the endpiece being adapted to at least partially inhibit disengagement of the plate spring from the extension as the user-accessible component is being depressed.

Alternate Embodiment D

The lancing device of alternative embodiment A, wherein the plate spring is comprised of a generally flexible material.

Alternate Embodiment E

The lancing device of alternative embodiment A further comprising at least two ramps forming a channel generally aligned with the aperture, the lancet holder being located within the channel formed by the ramps.

Alternate Embodiment F

The lancing device of alternative embodiment E, wherein the plate spring is adapted to engage the ramps.

Alternate Embodiment G

The lancing device of alternative embodiment E, wherein further depression of the user-accessible component in the second direction causes the ramps to allow the lancet holder to move toward the aperture in the direction opposite the first direction to a puncture position.

Alternate Embodiment H

The lancing device of alternative embodiment A, further comprising a pin located at least partially within the opening, the pin being adapted to associate with the activation mechanism, the activation mechanism being adapted to partially rotate around the pin upon depression of the user-accessible component.

Alternate Embodiment I

A lancing device, comprising:
a housing including a first end, a second end, and a first wall, the first end being adjacent to the first wall, the second end being adjacent to the first wall opposite the first end, the first end having an aperture extending therethrough, the first wall having an opening extending therethrough;
at least two ramps located within the housing, the at least two ramps forming a channel therebetween generally aligned with the aperture;
a lancet holder partially contained within the channel formed by the at least two ramps, the lancet holder being adapted to hold a lancet in a position generally aligned with the aperture;
a drive spring attached to and connecting the lancet holder and the second end of the housing, the drive spring being attached to the lancet holder opposite the aperture; and
an activation mechanism including a user-accessible component and a plate spring, at least a portion of the user-accessible component extending through the opening and being external to the housing, the plate spring being substantially located within the housing, the plate spring being adapted to engage the at least two ramps forming the channel as well as the lancet holder upon depression of the user-accessible component in the direction of the housing, wherein in response to depression of the user-accessible component, the lancet holder is adapted to move towards the second end to a cocked position and upon further depression of the user-accessible component, the lancet holder is adapted to move toward the first end to a puncture position.

Alternate Embodiment J

The lancing device of alternative embodiment I, wherein the plate spring is adapted to act as a dampening mechanism after the lancet holder has moved to the puncture position.

Alternate Embodiment K

The lancing device of alternative embodiment I, wherein the at least two ramps produce an audible sound as the lancet holder nears the cocked position.

Alternate Embodiment L

The lancing device of alternative embodiment I, wherein the ramps generally trend towards the first wall as the distance from the first end increases.

Alternate Embodiment M

The lancing device of alternative embodiment I, wherein the lancet holder includes an extension in the direction opposite the first end.

Alternate Embodiment N

The lancing device of alternative embodiment M, wherein the extension includes an endpiece adapted to at least partially inhibit disengagement of the plate spring.

Alternate Embodiment O

The lancing device of alternative embodiment I, wherein the at least two ramps at least partially assist in guiding the movement of the lancet holder.

Alternate Embodiment P

The lancing device of alternative embodiment I, wherein the lancing device is adapted to be operated by a single user action with a single hand.

Alternate Process Q

A method of using a lancing device comprising the acts of:
depressing an activation mechanism in a first direction, the activation mechanism including a user-accessible component and a plate spring;
moving a lancet holder in a second direction to a cocked position, the second direction being generally perpendicular to the first direction, the depression of the activation mechanism in the first direction causing the plate spring to engage the lancet holder; and
releasing the lancet holder, the release of the lancet holder allowing the lancet holder to move in a third direction to a puncture position, the third direction being opposite the second direction.

Alternate Process R

The method of alternative process Q, further comprising the act of dampening the lancet holder after the lancet bolder has moved to the puncture position, the dampening being assisted by the contact of the plate spring with the lancet holder as the lancet holder returns from the puncture position.

Alternate Process S

The method of alternative process Q, further comprising the act of producing an audible sound as the lancet holder moves to the cocked position.

Alternate Process T

The method of alternative process Q, wherein the release of the lancet holder is facilitated by a plurality of ramps adapted to disengage the plate spring from the lancet holder.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention as defined by the appended claims.

The invention claimed is:

1. A lancing device comprising:
a housing forming a central cavity including an aperture and an opening, the aperture including a central axis aligned in a first direction and the opening includes a central axis aligned in a second direction, the first direction being generally perpendicular to the second direction;
a lancet holder adapted to receive a lancet, the lancet holder being located within the central cavity formed by the housing, the lancet holder being adapted to maintain the lancet in a position generally aligned with the aperture in the first direction, the lancet being adapted to at least partially extend through the aperture;
at least two ramps forming a channel generally aligned with the aperture in the first direction, the lancet holder being located within the channel formed by the ramps;
a drive spring attached to and connecting the lancet holder and the housing, the drive spring being attached to the lancet holder opposite the aperture; and
an activating mechanism including a user-accessible component and a plate spring, at least a portion of the user-accessible component extending through the opening and being external to the housing, the user-accessible component being adapted to be depressed in the second direction towards the housing, the plate spring being adapted to engage the lancet holder upon depression of the user-accessible component in the second direction,
wherein the depression of the user-accessible component in the second direction causes the plate spring to move the lancet holder away from the aperture in the first direction to a cocked position.

2. The lancing device of claim 1, wherein the lancet holder includes an extension generally aligned with the first direction, the plate spring being adapted to engage the extension upon depression of the user-accessible component.

3. The lancing device of claim 2, wherein the extension includes an endpiece, the endpiece being adapted to at least partially inhibit disengagement of the plate spring from the extension as the user-accessible component is being depressed.

4. The lancing device of claim 1, wherein the plate spring is comprised of a generally flexible material.

5. The lancing device of claim 1, wherein the plate spring is adapted to engage the ramps.

6. The lancing device of claim 1, wherein further depression of the user-accessible component in the second direction causes the ramps to allow the lancet holder to move toward the aperture in the direction opposite the first direction to a puncture position.

7. A lancing device comprising:
- a housing forming a central cavity including an aperture and an opening, the aperture including an axis aligned in a first direction and the opening includes an axis aligned in a second direction, the first direction being generally perpendicular to the second direction;
- a lancet holder adapted to receive a lancet, the lancet holder being located within the central cavity formed by the housing, the lancet holder being adapted to maintain the lancet in a position generally aligned with the aperture, the lancet being adapted to at least partially extend through the aperture;
- a drive spring attached to and connecting the lancet holder and the housing, the drive spring being attached to the lancet holder opposite the aperture;
- an activating mechanism including a user-accessible component and a plate spring, at least a portion of the user-accessible component extending through the opening and being external to the housing, the user-accessible component being adapted to be depressed in the second direction towards the housing, the plate spring being adapted to engage the lancet holder upon depression of the user-accessible component in the second direction; and
- a pin located at least partially within the opening, the pin being adapted to associate with the activation mechanism, the activation mechanism being adapted to partially rotate around the pin upon depression of the user-accessible component,
- wherein the depression of the user-accessible component in the second direction causes the plate spring to move the lancet holder away from the aperture in the first direction to a cocked position.

8. A lancing device, comprising:
- a housing including a first end, a second end, and a first wall, the first end being adjacent to the first wall, the second end being adjacent to the first wall opposite the first end, the first end having an aperture extending therethrough, the first wall having an opening extending therethrough;
- at least two ramps located within the housing, the at least two ramps forming a channel therebetween generally aligned with the aperture;
- a lancet holder partially contained within the channel formed by the at least two ramps, the lancet holder being adapted to hold a lancet in a position generally aligned with the aperture;
- a drive spring attached to and connecting the lancet holder and the second end of the housing, the drive spring being attached to the lancet holder opposite the aperture; and
- an activation mechanism including a user-accessible component and a plate spring, at least a portion of the user-accessible component extending through the opening and being external to the housing, the plate spring being substantially located within the housing, the plate spring being adapted to engage the at least two ramps forming the channel as well as the lancet holder upon depression of the user-accessible component in the direction of the housing,
- wherein in response to depression of the user-accessible component, the lancet holder is adapted to move towards the second end to a cocked position and upon further depression of the user-accessible component, the lancet holder is adapted to move toward the first end to a puncture position.

9. The lancing device of claim 8, wherein the plate spring is adapted to act as a dampening mechanism after the lancet holder has moved to the puncture position.

10. The lancing device of claim 8, wherein the at least two ramps produce an audible sound as the lancet holder nears the cocked position.

11. The lancing device of claim 8, wherein the ramps generally trend towards the first wall as the distance from the first end increases.

12. The lancing device of claim 8, wherein the lancet holder includes an extension in the direction opposite the first end.

13. The lancing device of claim 12, wherein the extension includes an endpiece adapted to at least partially inhibit disengagement of the plate spring.

14. The lancing device of claim 8, wherein the at least two ramps at least partially assist in guiding the movement of the lancet holder.

15. The lancing device of claim 8, wherein the lancing device is adapted to be operated by a single user action with a single hand.

* * * * *